US005857968A

United States Patent [19]

Benja-Athon

[11] Patent Number: 5,857,968
[45] Date of Patent: Jan. 12, 1999

[54] COUPLING DEVICE IN ELECTROACUPUNCTURE

[76] Inventor: Anuthep Benja-Athon, 210 E. 36th St. Ground Floor, New York, N.Y. 10016

[21] Appl. No.: 976,585

[22] Filed: Nov. 24, 1997

[51] Int. Cl.[6] .......... A61B 17/34
[52] U.S. Cl. .......... 600/372
[58] Field of Search .......... 600/372, 373, 600/377, 382; 607/46; 606/189; 128/907

[56] References Cited

U.S. PATENT DOCUMENTS

| | | | |
|---|---|---|---|
| 4,262,672 | 4/1981 | Kief | 607/46 |
| 4,580,566 | 4/1986 | Hsu | 606/189 |
| 4,950,279 | 8/1990 | Chang | 606/189 |
| 4,989,604 | 2/1991 | Fang | 128/907 |
| 5,094,242 | 3/1992 | Gleason et al. | 600/377 |

*Primary Examiner*—George Manuel

[57] ABSTRACT

A first independent electricity-conductive cradle comprises a visual-enhancement materials and a continuation of the electricity conducting electrical lead on the floor of the cradle and within an electricity conductive strip in said cradle adaptable to be introduced to and fit the handle of a second independent, percutaneously implanted metallic electro-acupuncture needle and pin thereby results in an excessively-tight coupling of said cradle and handle for affixing said electrical lead to the electricity conductive means of said handle in electroacupuncture to either reduce the risk or eliminate the transmission of infection and diseases. The continuation of the electricity conductive material of the shaft member is the handle of the acupuncture needle and pin and also on and along the wall of the handle. The excessively-tight linkage of the cradle and the handle ensures the optimal contact of the electrical lead and the needle and pin, and, therefore, the flow of the electricity from the electrical lead, the strip, cradle, handle, the continuation of the shaft, the shaft of the acupuncture needle to the person. Adhesive on one wall of the cradle permits reversible attachment of the cradle to the skin during electroacupuncture. The cradle and handle contain visualization enhancement materials to increase visualization and spatial localization of the handle and the cradle. The excessively tight coupling compels the disposal of the acupuncture pin and electrical lead after one single use.

11 Claims, 3 Drawing Sheets

COUPLING DEVICE IN ELECTROACUPUNCTURE

FIELD OF INVENTION

Coupling device incorporating visualization enhancement materials and adhesive substance to reduce or eliminate the transmission of diseases in electroacupuncture.

BACKGROUND OF THE INVENTION

The first objective is to provide a coupling device in electroacupuncture to eliminate the transmission of infectious organisms such as bacteria, virus, fungus between patients and acupuncturists in electroacupuncture.

The second objective is to provide single-use, disposable, recyclable electrical lead and, therefore, compel the disposable of all instruments including the electrical lead after the application on a patient in electro-acupuncture.

The third objective is to provide an easy-to- use, effective, reliable, fixed, i.e. immovable, coupling of the electrical lead and acupuncture needle and pin to ensure the ease of application and to achieve the above objectives.

The fourth objective is to provide effective, optimal, and reliable electrical connection and contact between the electrical lead and the acupuncture needle and, therefore, ensuring the correct and optimal delivery of electrical current from the electrical lead to the acupuncture needle and pin in electroacupuncture. "Acupuncture has been used by millions of American patients and performed by thousands of physicians, dentists, acupuncturists, and other practitioners for relief of prevention of pain and for a variety of health conditions." (National Institutes of Health Consensus Development Statement. Acupuncture. Nov. 3–5, 1997). The United States Food and Drug Administration has classified acupuncture pin as a medical device. The approval and consensus have resulted in tremendous growth of the application of acupuncture therapeutics by American acupuncturists.

LACK OF STERILE EQUIPMENT AND TECHNIQUE: Transmission of infections and diseases in electroacupuncture between patients and acupuncturists is well documented in the scientific literature (Ernst E. et al. Life-threatening adverse reactions after acupuncture? A systematic review. Pain 71: 123–126, 1997). Two of the reasons are that there is a lack of sterile equipment and technique and the disregards for using sterile equipment and technique. The design deficiency of the prior art of acupuncture pin and equipment significantly contributed to aforementioned problems.

Presently , electroacupuncture using the micron-thick shaft of a metallic needle and pin being grasped by a relatively larger alligator clip of one end of an electrical lead are the most commonly tools used in America. Essentially, an acupuncture needle has a handle and a shaft with a bore and an acupuncture pin has a handle and a solid shaft. The electrical lead of prior art consisting of a plastic-insulated wire with one end connects to a grasping device such as an alligator clip and the opposite end connected to the electrical stimulator. To establish the flow of electrical current from the electrical lead to the shaft of the acupuncture needle, the alligator clip grasps onto the micron-thick shaft of the acupuncture needle for the purpose of transmitting electrical current from the stimulator via the wire, the grasping device, the acupuncture pin, into the patient.

First, the connection between alligator clip and the micron-thick shaft of the acupuncture needle and pin is loose and poor. The alligator clip is not designed for the purpose of grasping the micron-thin shaft of the acupuncture needle and pin whose diameter is too small to be effectively grasped by the alligator clip. As a result, unreliable delivery of correct ampere and voltage of the electrical current to the acupuncture needle and pin are common. Second, the contact parts of the alligator clip, after so many use, are often oxidized rendering the clip ineffective due to a barrier of a layer of nonconductive oxidized matters.

Breaching of the sterile technique is common. First, the alligator clip and the electrical lead, which are not sterile to start, will not fix to one position site of the shaft of the acupuncture needle and pin and will slide toward the acupuncture site of the skin during the application of the electrical lead leading to the contamination of the acupuncture skin site and, consequently, the transmission of infectious organisms via the acupuncture site of the skin. Second, the electrical lead and the alligator clip are reused from patient to patient. Eventhough the acupuncture needle and pin are sterile, the alligator clip and its electrical lead are not sterile.

The connection of acupuncture and alligator clip tend to swing loosely in the air without a means of attaching both instruments to the skin and, consequently, causing the weight of the electrical lead to easily dislodge the percutaneously implanted acupuncture needle and pin and exposing the sharp tip of the acupuncture needle and pin to inadvertently puncture the fingers of the acupuncturists resulting in the transmission of diseases in electroacupuncture.

The acupuncture needle and pin and, therefore, the sharp tip of the shaft are difficult to visualize especially in the clinical settings and, consequently, inadvertent puncture of the fingers of the acupuncturists is common leading to the transmission of diseases in electroacupuncture.

In brief, the design deficiency of the acupuncture needle and pin and the electrical lead of prior art promotes the transmission infection and diseases between patients and acupuncturists. The present invention solves the aforementioned problems.

SUMMARY OF THE INVENTION

The design deficiency of the prior art of acupuncture pin and equipment significantly contributed to transmission of infections and diseases in electroacupuncture between patients and acupuncturists.

The present invention provides a cradle at one end of an electrical lead for excessively tight and immovable coupling of an acupuncture needle handle to reduce the risk of and eliminate the transmission of diseases in electroacupuncture. The continuation of the shaft member of the acupuncture needle is on and along the wall of the handle. The cradle having the continuation of the electrical lead in the cradle's floor. The linkage of the handle and the cradle ensures optimal contact of aforementioned cradle and handle and their members and, therefore, ensures the flow of the electricity from the electrical lead via the cradle, handle, and the continuation of the electrical conduction members into the shaft of the acupuncture needle. Adhesive on one wall of the cradle permits attaching of the above coupled handle-cradle to the skin during electroacupuncture. The handle and cradle contain visualization enhancement materials which are incorporated into the materials use to make the handle and the cradle. The visualization enhancement materials, are such as, but not limited to fluorescence, light-sensitive, light-activated, and light-reflective materials to increase visualization and spatial localization of the handle, and therefore, the acupuncture needle and pin and their sharp tip, and the cradle. The aforementioned excessively tight coupling compels the acupuncturist to discard the used acupuncture needle and pin and the electrical lead after one single use on a patient.

PREFERRED EMBODIMENTS OF THE INVENTION

Figure 1:
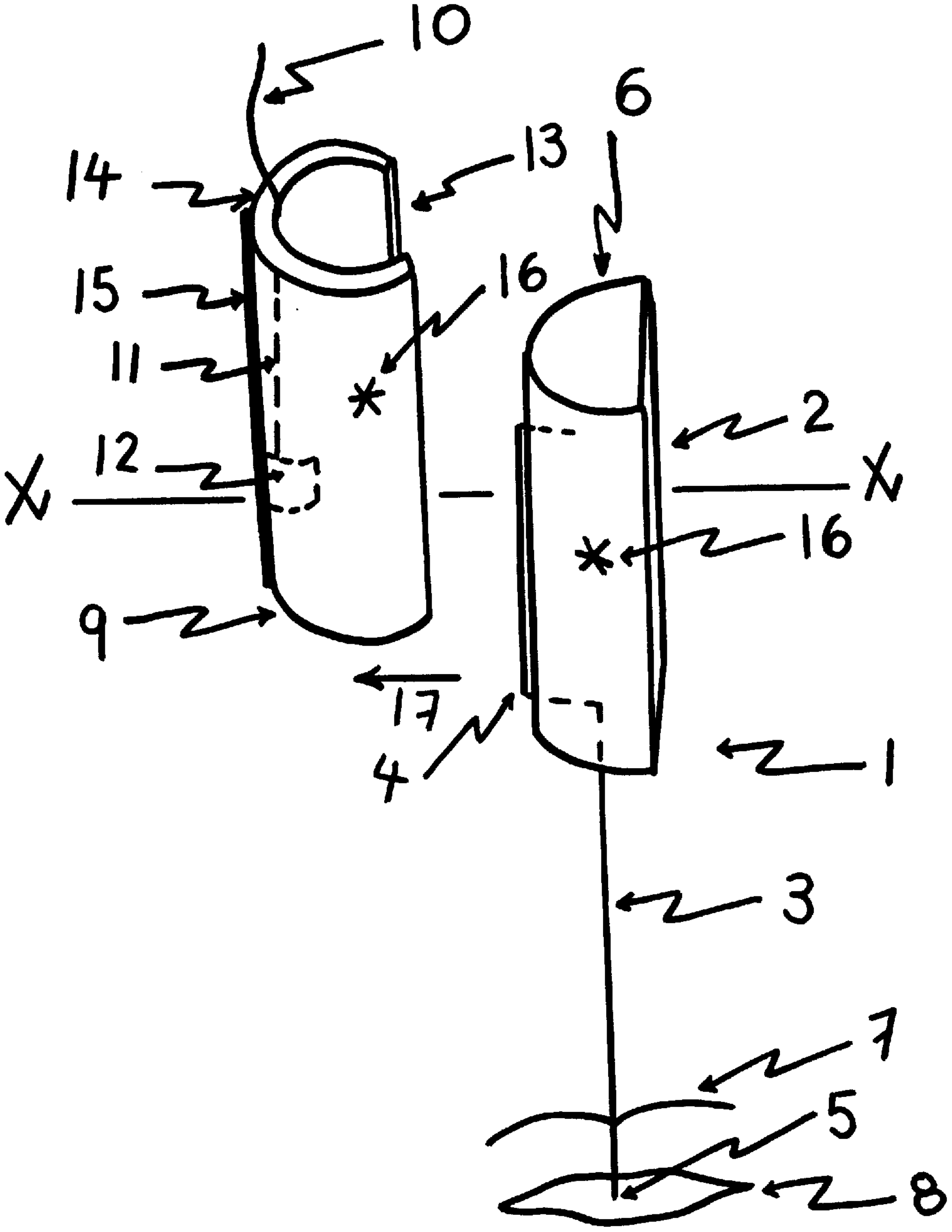
FIG. 1 is a perspective view of the present invention prior to coupling.

FIG. 1 shows, with strict sterile surgical technique, the acupuncture needle 1 which comprises of handle 2 and shaft 3 was percutaneously inserts through skin 7 of a patient. The tip 8 of shaft 3 is positioned in the final desire position in the soft tissues 8 of the patient. On and along the wall of handle 2 of acupuncture needle 1 is the continuation of the electrical conduction 4 of shaft 3. Handle 2 has its contour 6 for the purpose of excessively tight fitting with cradle 9.

FIG. 1 shows cradle 9 at one end of an electrical lead 10. The continuation of the electrical conduction 11 of electrical lead 10 is on the inner wall of cradle 9 and ends in strip 12 which is also on the inner wall of cradle 9. The contour of cradle 9 is a ¾-circular trough 13 which allows the excessively tight complimentary fitting of contour 6 of the wall of handle 2. The excessively tight complimentary fitting (shown in FIG. 3) of handle 2 and cradle 9 is achieved by snapping handle 2 into cradle 9 by a motion as represents by straight single arrow 17.

FIG. 1 further shows adhesive 15 on one of the outer wall 14 of cradle 9 so that when coupled handle 2-cradle 9 can be reversibly attached and secured to skin 7 of a patient during the electroacupuncture therapeutics.

FIG. 1 further shows handle 2 and cradle 9 contain visualization enhancement materials 16 such as, but not limited to, fluorescence, light-sensitive, light-activated, and light-reflective materials to increase the visualization and spatial localization and orientation of the handle 2 and cradle 9. The visualization enhancement materials 16 is integrated into the entire handle 2 and cradle 9.

Figure 2:
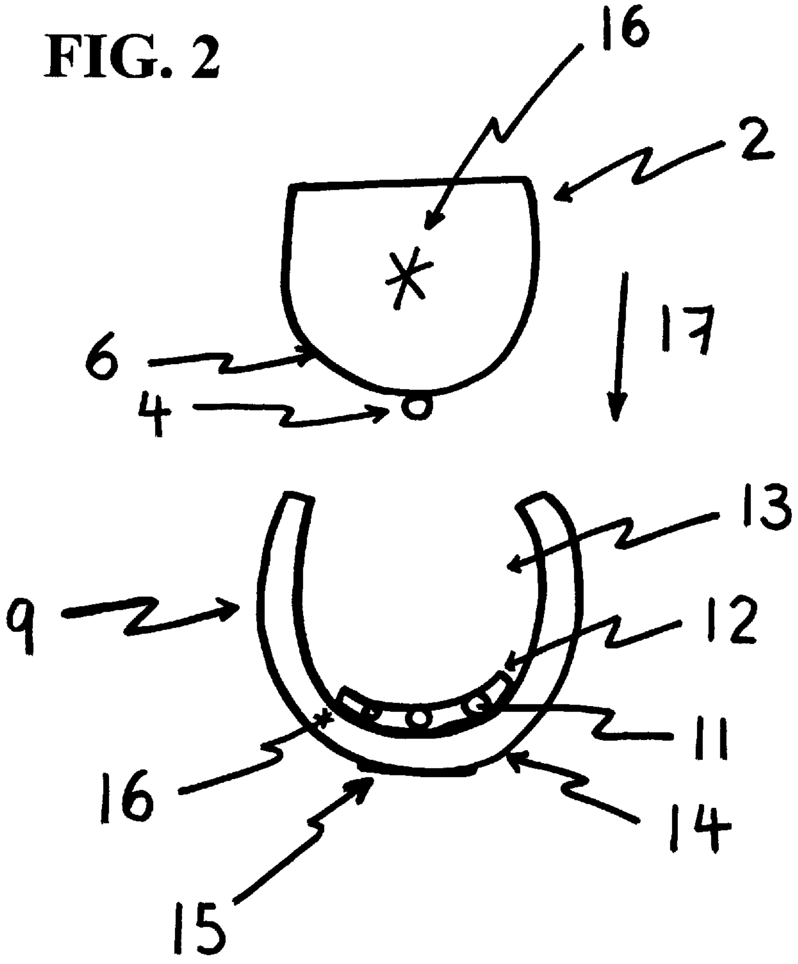
FIG. 2 is a schematic view of the present invention at section 26 in FIG. 2.
Figure 3:
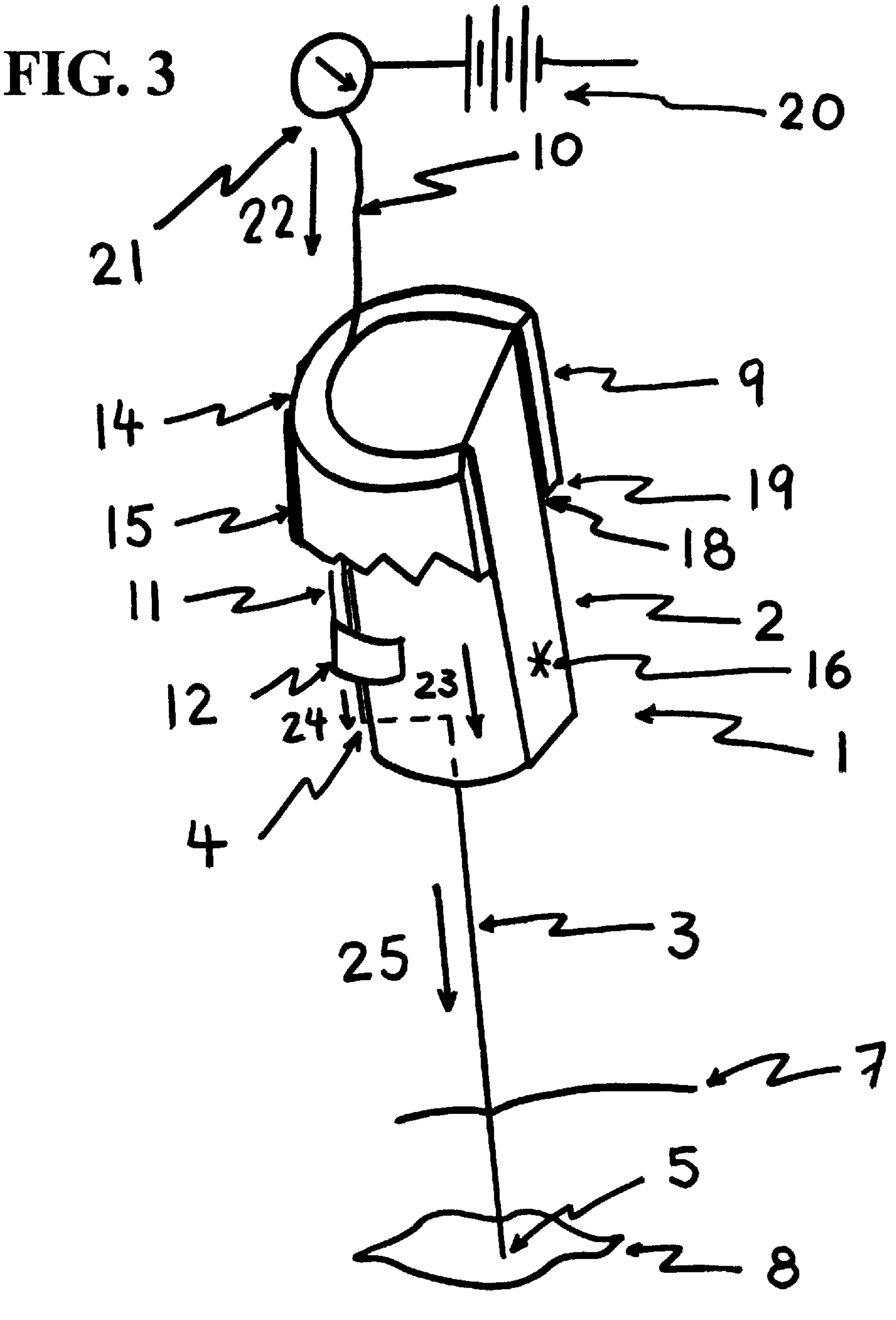
FIG. 3 is a perspective view of the present invention at coupling.

FIG. 2 shows the cross section 26 in FIG. 1 of handle 2 and cradle 9 prior to excessively tight coupling 18 (shown in FIG. 3). The snap-in movement as represents by straight single arrow 17 of handle 2 into cradle 9 resulting in excessively tight coupling 18 and optimal contact between cradle 9, handle 2, continuation of shaft 4, and continuation of electrical lead 11, and strip 12.

FIG. 3 shows the excessively tight coupling 18 of the handle 2 of acupuncture pin 1 to the cradle 9 forming a fix and immovable coupling at a precisely intended and definite position on handle 2 of acupuncture pin 1. A cut-away cradle 19 shows the relationship, i.e. optimal contact, between cradle 9, handle 2, continuation of shaft 4, and continuation of electrical lead 11, and strip 12. Electricity producer 20 supplies electricity flowing in electrical lead 10 as represents by single straight arrow 22. The flowing electricity from electrical lead 10 flows into cradle 9, continuation of electrical lead 11, strip 12 and into handle 2 as represents by single straight arrow 23. Also the flowing electricity from electrical lead 10 flows into cradle 9, continuation of electrical lead 11, strip 12 and into continuation of shaft 4 as represents by single straight arrow 24. The electricity then passes into shaft 3 as represents by single straight arrow 25.

An ammeter 21 registered the change and flux in electrical current as the acupuncture needle passes through various and different types of tissues possessing different electrical resistance in the body of a patient.

After the electroacupuncture therapeutics, the acupuncture needle is withdrawn from the skin and removed from the body of the patient. Because of the excessively tight coupling 18 of handle 2 of acupuncture needle 1 to cradle 9, the acupuncture needle 1 is not separable from cradle 9 and, consequently, the entire coupled handle 2-cradle 9 is discarded as one single unit. Therefore, no reuse of the electrical lead and the acupuncture needle is allowed.

Although various preferred embodiments of this invention have been described, it will be appreciated by those skilled in the art that variations may be made without departing from the spirit of the invention or the scope of the claims.

I claim:

1. A first independent electricity-conductive cradle incorporates a visual-enhancement means and a continuation of the electricity conducting means of an electrical lead on and ending within an electricity conductive strip means on the floor of said cradle adaptable to be introduced to and fit the handle of a second independent, metallic electro-acupuncture needle and pin having the shaft means percutaneously implanted in the tissues of a person thereby results in an excessively-tight coupling of said cradle and handle for affixing said electrical lead to the electricity-conductive means of said handle in electroacupuncture to either reduce the risk or eliminate the transmission of infection and diseases comprising:

connection means;

contact means for the flow of electrical current;

adhesive means; and visualization enhancement means.

2. The cradle and electro-acupuncture needle and pin according to claim 1 wherein said connection means is the handle of said acupuncture needle and pin.

3. The cradle and electro-acupuncture needle and pin according to claim 1 wherein said connection means is said cradle which is a ¾-circular trough adaptable to fit to said handle.

4. The cradle and electro-acupuncture needle and pin according to claim 1 wherein said contact means for the flow of electrical current is said electricity-conductive cradle.

5. The cradle and electro-acupuncture needle and pin according to claim 1 wherein said contact means for the flow of electrical current is the electrical lead housed on the floor of said cradle.

6. The cradle and electro-acupuncture needle and pin according to claim 1 wherein said contact means for the flow of electrical current is the electricity-conductive strip means on the floor of said cradle.

7. The cradle and electro-acupuncture needle and pin according to claim 1 wherein said contact means for the flow of electrical current is the electricity-conductive handle means of said needle and pin.

8. The cradle and electro-acupuncture needle and pin according to claim 1 wherein said contact means for the flow of electrical current is the electricity-conductive continuation of the shaft on the outer wall of said handle.

9. The cradle and electro-acupuncture needle and pin according to claim 1 wherein said adhesive means is the adhesive on one outside wall of said cradle adaptable to reversibly attach said cradle to the skin.

10. The cradle according to claim 1 wherein said visualization enhancement means is incorporated into said cradle comprises light-emitting substance, light-sensitive substance, light-activated substance, and light-reflective substance.

11. A visualization enhancement means incorporates into the electricity-conductive handle of a second independent metallic electro-acupuncture needle and pin adaptable to snap into and fit a first independent electricity-conductive cradle comprising a visual-enhancement means and a continuation of the electricity conducting means of an electrical lead on and ending within an electricity conductive strip means on the floor of said cradle in electroacupuncture to either reduce the risk or eliminate the transmission of infection and diseases comprising:

light-emitting substance;

fluorescence;

light-sensitive substance;

light-activated substance; and light-reflective substance.

* * * * *